United States Patent [19]
Ehrenberger et al.

[11] Patent Number: 5,563,140
[45] Date of Patent: Oct. 8, 1996

[54] USE OF 1-(AMINOALKYL)-3-(BENZYL)-QUINOXALINE-2-ONE DERIVATIVES FOR THE PREPARATION OF NEUROPROTECTIVE COMPOSITIONS

[75] Inventors: Klaus Ehrenberger, Vienna, Austria; Dominik Felix, Zurich, Switzerland

[73] Assignee: Phafag Aktiengesellschaft, Schaan, Liechtenstein

[21] Appl. No.: 975,328

[22] Filed: Nov. 16, 1992

[30] Foreign Application Priority Data

Nov. 15, 1991 [EP] European Pat. Off. ............... 91119501

[51] Int. Cl.$^6$ ................... A61K 31/55; A61K 31/495; A61K 31/50
[52] U.S. Cl. ............................. 514/249; 514/212
[58] Field of Search ................... 514/410, 212, 514/249

[56] References Cited

U.S. PATENT DOCUMENTS 5,037,848   8/1991   Olney ................................ 514/428

FOREIGN PATENT DOCUMENTS 0032564      7/1981   European Pat. Off. .
228204       7/1963   Germany .
WO90/15606   12/1990  WIPO .

OTHER PUBLICATIONS

"Studies of experimental cerebral artery dilatation (with caroverin fumarate", *Neurological Surgery*, Abstracts of the 7th International Congress of Neurological Surgery, Munich, Germany (Jul. 12–18, 1981), Supplement to Neurochirugia, Abstract No. 8.3.1, vol. 0, No. SU, p. 332, J. O. Widauer.
B. Meldrum, "Excitatory amino acid neurotoxicity and neurodegenerative disease", *Trends in Pharmacological Sciences*, vol. 11, No. 9 (Sep. 1990), pp. 379–387.
M. Ishida et al, "Reduction of glutamate responses at the crayfish neuromuscular junction", *Brain Research*, vol. 266, No. 1 (Apr. 25, 1983), pp. 174–177.
Y. Kudo et al, "Effects of caroverine and diltiazem on synaptic responses, L-glutamate-induced depolarization and potassium efflux in the frog spinal cord", *British Journal of Pharmacology*, vol. 83, No. 3 (Nov. 1984), pp. 813–820.
H. Shinozaki, "Pharmacology of the Glutamate Receptor", *Progress in Technology*, vol. 30 (1988), pp. 399–435.

Kessler et al, "Quinoxaline derivatives are high-affinity antagonists of the NMDA receptor-associated glycine sites", *Brain Research*, vol. 489 (1989), pp. 377–382.
A. Mule et al, "Terz-amminoalchilderivati di chinossalinoni ad attivita analgesica", *Il Farmaco Edizione Scientifica*, vol. 43, No. 7–8 (Aug. 1988), pp. 613–618.
Subsidia Medica, 22, 3, pp. 78–85 (1970).
Koppi et al, "Calcium-Channel-Blocking Agent in the Treatment of Acute Alcohol Withdrawal—Caroverine versus Meprobamate in a Randomized Double-Blind Study", *Neuropsychobiology*, 17, pp. 49–52 (1987).
Presslich et al, "Oesterreichische Apothekerzeitung", 38/39, p. 757 (1984).
Honore et al, "Quinoxalinediones: Potent Competitive Non-NMDA Glutamate Receptor Antagonists", *Science*, 241, pp. 701–703 (1988).
Merck Index, 11th Ed., 1989, #1864.
CA 99:3359, Ishida et al., 1983.
Kaplan *Clinical Hypertension* p. 235 1986.
Merck Manual p. 1308–1309; 1324–1327 1982.

*Primary Examiner*—Kimberly Jordan
*Attorney, Agent, or Firm*—Millen, White, Zelano, & Branigan, P.C.

[57] ABSTRACT

Compounds of the formula

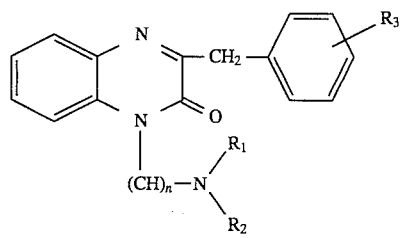

wherein $R_1$ and $R_2$ are each independently hydrogen, methyl, ethyl, propyl, butyl or $R_1$ and $R_2$ are together cycloalkyl;

$R_3$ is methoxy, ethoxy, hydroxy, hydrogen, $C_{1-4}$ alkyl, halogen;

n=1, 2 or 3;

or any pharmaceutically acceptable salts thereof are useful for the preparation of neuroprotective pharmaceutical compositions, for the prevention or treatment of glutamate-induced and glutamate receptor mediated neurotoxicity and functional disturbances of the central nervous system.

16 Claims, 3 Drawing Sheets

DURING Glu 15

USE OF 1-(AMINOALKYL)-3-(BENZYL)-QUINOXALINE-2-ONE DERIVATIVES FOR THE PREPARATION OF NEUROPROTECTIVE COMPOSITIONS

The present invention relates to the novel use of 1-(aminoalkyl)-3-(benzyl)-quinoxaline-2-one derivatives and pharmaceutically acceptable salts thereof for the preparation of neuroprotective pharmaceutical compositions.

Compounds of the formula

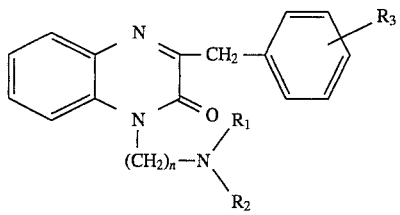

wherein $R_1$ and $R_2$ are each independently hydrogen, methyl, ethyl, propyl, butyl, or $R_1$ and $R_2$ are together cycloalkyl (e.g., of 3–7 C-atoms);

$R_3$ is methoxy, ethoxy, hydroxy, hydrogen, $C_1$–$C_4$ alkyl, halogen (e.g., F, Cl, Br or I);

n=1, 2 or 3, hereinafter referred to as 1-(aminoalkyl)-3-(benzyl)-quinoxaline-2-one derivatives, have been known for more than three decades (OE-A-228 204). 1-(Aminoalkyl)-3-substituted-quinoxaline-2-one derivatives which have in the 3-position a benzyl residue show a papaverine-like activity. (1-Diethylaminoethyl)-3-(p-methoxybenzyl)-1,2-dihydroquinoxaline-2-one with the International Non-Proprietary-name (INN) Caroverine, a member of the above class, was discovered to be a powerful spasmolyticum, which is used mainly in the gastrointestinal region. The efficacy of Caroverine is attributed to its calcium-blocking capacities whereby it blocks the calcium mediated activation of myofibrillar ATPase, predominantly in smooth muscles.

In EP-A 032 564 the use of Caroverine-fumarate for the inhibition of the aggregation of platelets in blood, increase of the arterial circulation, treating of ischemic heart diseases, angina pectoris, etc. was described. In addition, specific Caroverine salts had i.a. a positive effect on the cerebral blood circulation. It was also found that Caroverine is a specific Ca-antagonist (EP-A 032 564; page 18): The cardiac muscles and the smooth muscles contract under the influence of calcium ions. The Ca-ions enter the muscle cells through specific calcium channels and induce the contracting process from the inner cell. The calcium channels can be opened either by local voltage changes (voltage gated ionic channels), tissue hormones or by the transmitter adrenalin. It has been found that Caroverine is capable of inhibiting 50% of the flux of Ca-ions into the cell via "voltage gated channels" opened by electrical stimulation (EP-A 032 564; page 18). The influence of calcium on the chemical calcium-channels has not been examined.

Widauer studied the effect of Caroverine fumarate on cerebral artery dilatation (Neurological Surger, suppl. to Neurochirurgia, 1981, p. 332, abstract no. 8.3.1). He, too, attributed the effect of Caroverine to its role as Ca-antagonist.

In Subsidia med. 22, 3, pp. 78–85 (1970) Möslinger reported that Caroverine could suppress epileptic seizures, even status epilepticus. Recent investigations describe (Koppi et al in Neuropsychobiology 17, pp. 49–52, 1987) the use of Caroverine in treatment of acute alcohol withdrawal symptoms. Koppi et al were inspired by Presslich and Brainin (Oesterreichische Apothekerzeitung 38/39, p. 757 (1984)) who has tested Caroverine during alkaloid withdrawal.

In contrast to the cited publications the present invention is based on the surprising discovery of 1-(aminoalkyl)-3-(benzyl)-quinoxaline-2-one derivatives as potent, selective and reversible glutamate receptor antagonists in the excitatory neurotransmission in the central nervous system.

Glutamate is the most abundant and important excitatory neurotransmitter in the central nervous system (Brien Meldrum in Emerging Strategies in Neuroprotection, edited by P. J. Marangos and Harbans Lal, Birkhäuser Boston, 1992, chapter 7). In the central nervous system, glutamate functions to promote rapid neurotransmitter depolarization by opening membrane channels chemically (in contrast to the voltage-gated inhibition of $Ca^{++}$-influx in smooth muscle cells) which permit diffusion of sodium and calcium ions. These fast effects are mediated by different glutamate-sensitive receptor types which act as a specific "central key/lock system" and permit excitation of the subsequent nerve cell.

The glutamate receptors are extremely sensitive to a wide range of external damage (noxae), such as injuries, oxygen deficiency, metabolic disturbances, aging processes, etc., and, under these conditions, lead to a specific kind of overstimulation of the subsequent nerve cell.

Under the conditions of an excessive stimulation of the receptors, the physiological transmitter glutamate exerts a neurotoxic action (Rothman et al in Trends Neurosci. 10 (1987), pp. 299–302). This excitotoxicity is mediated by the receptors N-methyl-D-aspartate (NMDA) as well as by the two non-NMDA subtypes, quisqualate and kainate (Frandsen et al, J. Neurochem. 53 (1990), pp. 297–299), whereby Ca is involved in the etiology of the glutamate-induced cell damage which can finally result in the death of the affected neurons. (Choi, Trends Neurosc., 11 (1988), pp. 465–469). This glutamate receptor-linked neurotoxicity has been implicated in pathological conditions like ischemia, hypoglycemia, anoxia, trauma and several severe neurodegenerative disorders (Meldrum et al, Trends pharmacol. Sci. 11(1990), pp. 379–387) as well as in neuronal death in aging. In vitro and in vivo, glutamate receptor antagonists, as neuroprotective agents, can prevent these pathological conditions.

Therefore, there is a great interest in the development of new drugs that might selectively block the NMDA and non-NMDA receptors without influencing other receptors since such drugs could be used as neuroprotective pharmaceuticals. Applications of these pharmaceuticals could be the treatment of glutamate-induced and glutamate-receptor-mediated neurotoxic dysfunctions such as functional disturbances of the inner ear, like tinnitus and impaired hearing, and of the retina, (post)traumatic lesions, and degenerative processes of neurons in the central nervous system like Alzheimer's, Parkinson's disease, etc. (Akhlaq et al, Brain Research Reviews, 16 (1991), pp. 171–191). Reversibility is also a highly desired characteristic since a return to normal function after preventing a therapeutic function is desired.

Thus, the invention involves the use of compounds of the formula

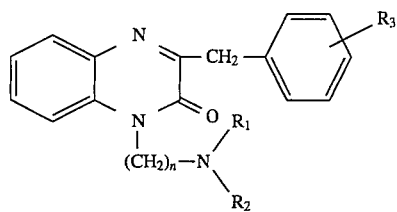

wherein $R_1$ and $R_2$ are each independently hydrogen, methyl, ethyl, propyl, butyl or $R^1$ and $R_2$ together are cycloalkyl;

$R_3$ is methoxy, ethoxy, hydroxy, hydrogen, $C_1$–$C_4$ alkyl, or halogen and n=1, 2 or 3;

or a pharmaceutically acceptable salt thereof, for the preparation of neuroprotective compositions for the prevention or treatment of neurotoxicity and functional disturbances of the central nervous system with the exception of diseases like epileptic seizures and alcohol withdrawal symptoms.

Among the presently known antagonistic substances are 6-cyano-7-nitroquinoxaline-2,3-dione (CNQX) and 6,7-dinitroquinoxaline-2,3-dione (DNQX) (Honore et al in Science 241, pp. 701=703 (1988)). DNQX and CNQX are at submicromolar concentrations competitive non-NMDA receptor antagonists binding to quisqualate receptors and at somewhat higher concentrations block the effect of NMDA receptors (Kessler et al, Brain Research 489, pp. 377–382). However, CNQX and DNQX can also act as non-competitive antagonists inhibiting the strychnine-insensitive NMDA-associated glycine recognition site meaning that important vital processes are disrupted by these compounds. Therefore, a pharmaceutical use of CNQX and DNQX is not feasible.

Ishida et al (Brain Research, 266 (1983) pp. 174–177) studied the effect of Caroverine at the crayfish neuromuscular junction. They reasoned that Caroverine might be an open channel blocker for glutamate. Their findings, however, were rather contradictory as they did not find a Caroverine effect under more realistic, physiological conditions. Further investigations by Kudo and Shibata (Br. J. Pharmac. (1984), 83, pp. 813–820) published one year later led to the opinion that Caroverine was an unspecific calcium-channel-blocking agent but not a glutamate antagonist. They also found that the effect on glutamate does not take place at its receptors.

The present invention is based upon results received by examining the effects of 1-(aminoalkyl)-3-(benzyl)-quinoxaline-2-one derivatives directly in the mammalian cochlea and upon subsequent clinical studies.

In the mammalian cochlea, there is strong evidence that two classes of glutamate-receptors, the N-methyl-D-aspartate (NMDA) subclass and the non-NMDA subclass, comprising the quisqualate and kainate subtypes, mediate postsynaptic glutamatergic neurotransmission between the inner hair cells (IHC) and the peripheral dendrites of the afferent neurons (Puel et al, Hear. Res., 51, (1991), pp. 255–264). Using physiological techniques, up to now, no other types of receptor channels could be found at the IHC synapses. Therefore, the IHC synapse is an elegant and easily accessible model for prominent excitatory synapses corresponding to similar structures of the central nervous system (CNS) since the physiological structures and mechanisms in the cochlea correspond to similar structures and mechanisms in the central nervous system. These findings are therefore representative for similar synaptic connections of the central nervous system.

The effectiveness of the 1-(aminoalkyl)-3-(benzyl)-quinoxaline-2-one derivatives as potential glutamate receptor antagonists was studied in the light of the neurotransmission between the inner hair cells (IHC) and the peripheral dendrites of the afferent neurons in the mammalian cochlea.

Experiments were performed on adult pigmented guinea pigs (300–700 g) of both sexes, anaesthetized with a combination of Rompun (Bayer, Leverkusen, Germany) and Innovar-Vet (Pitman-Moore, Mundelin, Ill., U.S.A.). Supplementary low doses of pentobarbital (Nembutal, Abbott, Chicago, U.S.A.) were given periodically throughout the experiments. Rectal temperature was maintained within physiological limits. After tracheotomy for artificial respiration, the auditory bulla was approached ventrolaterally and the cochlea was exposed. A small opening was drilled into the cochlea bone over the pigmented stria vascularis and the ligamentum spiale of the third turn.

Multibarrel microelectrodes with overall tip diameter of 1.5–2 µm were inserted and microdriven almost parallel to the tectorial membrane until the subsynaptic region of the IHC layer was reached at a depth of 200–260 µm. The occurrence of phasic activity was used to identify the location precisely, since such activity occurs in the immediate vicinity of the initial postsynaptic structures.

Recordings of extracellular action potentials were obtained using a 2M NaCl-filled barrel of the 5-barrel glass micropipette. Recordings were analyzed on a rate meter (NE 4667) and displayed continuously on a UV-oscillograph (Bell & Howell 5–137). Three other channels of the micropipette contained the solutions to be ejected microiontophoretically with the appropriate anionic and cationic currents: L-glutamic acid (0.5M, pH 3.5, adjusted with HCl); Caroverine-HCl (1-diethylaminoethyl-3-(p-methoxybenzyl)-1,2-dihydro-quinoxaline-2-one, 0.05M, natural pH=6.0).

In order to avoid electrically induced artefacts, compensation currents were applied through an NaCl-filled channel. Correct positioning of the tip of the micropipette in the synaptic region of the IHC's resulted in a spontaneous phasic activity characterized by graded potentials. Glutamate, the agonist of NMDA and non-NMDA receptors, enhances the firing rate in the majority of the fibers tested (n=29 out of 31).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application EPA 91 119 501.4 of Nov. 15, 1991 are hereby incorporated by reference.

BRIEF DESCRIPTION OF THE DRAWINGS

The experimental results are now explained with reference to the drawings.

Figure 2:
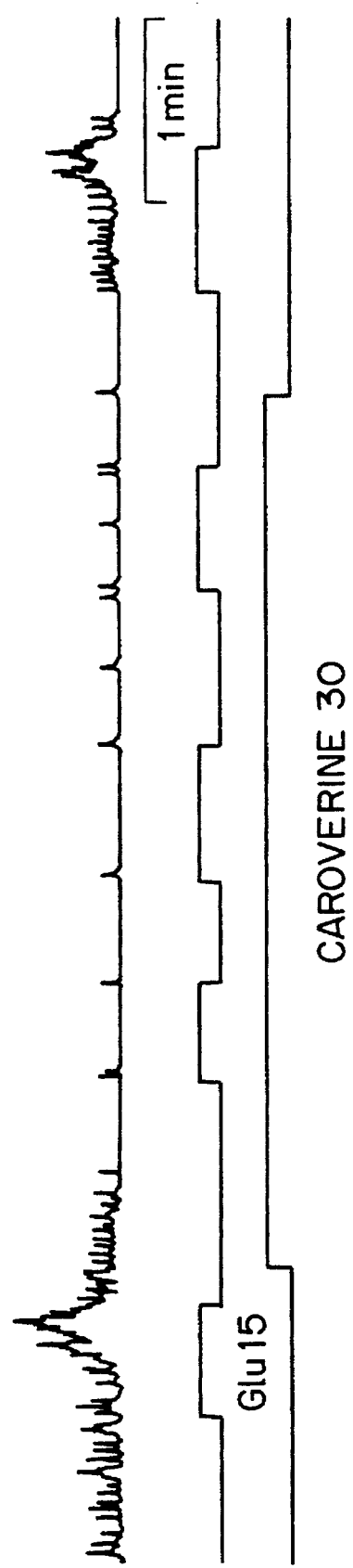
Figure 3:
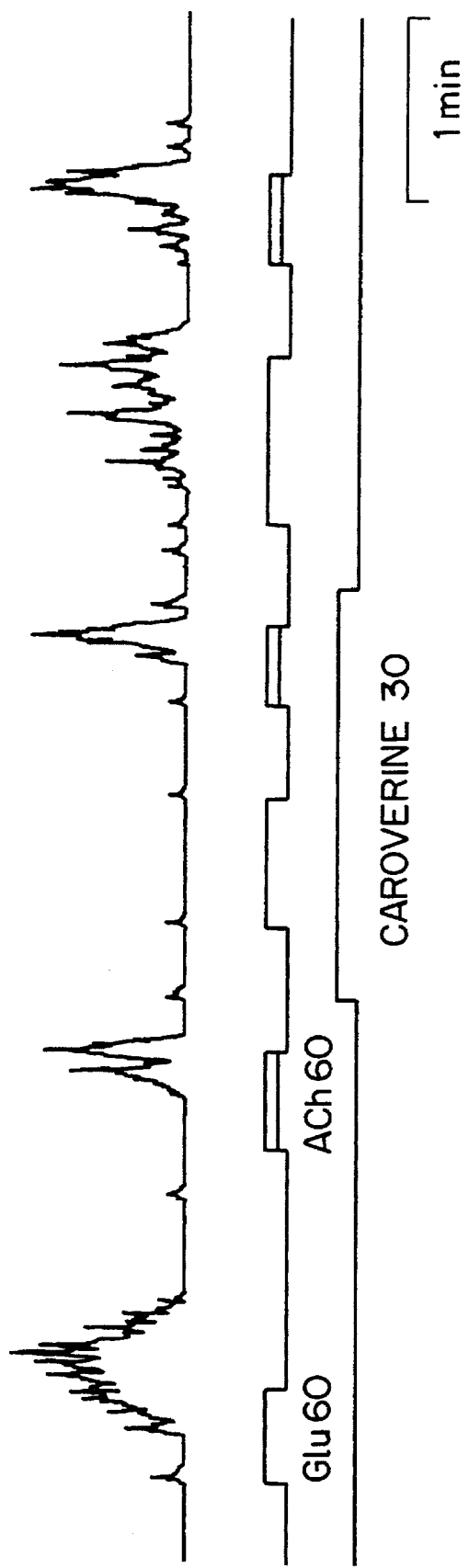

b) the same glutamate-induced irregular spike-activity characterized by bursts, illustrated on an original oscilloscope trace (calibrations: 20 msec, 1 mv);

FIG. 2 shows the effect of Caroverine on glutamate-induced spike-activity, demonstrated on time frequency histograms. The excitatory action of L-glutamate (Glu, 15 nA) is blocked by Caroverine (30 nA for about 5 minutes) in a potent but reversible manner;

FIG. 3 shows the neural response to a four times higher amount of L-glutamate (Glu, 60 nA) and the same amount of acetylcholine (Ach, 60 nA) before, during and after ejection of Caroverine, using the same amount as in FIG. 2 (Caroverine, 30 nA). Caroverine selectively blocks the glutamate action whereas the acetylcholine-induced firing rate remains unaffected. The ejection periods of substances ejected from the same micropipette at the same synapse are indicated by different bars.

Figure 1A:
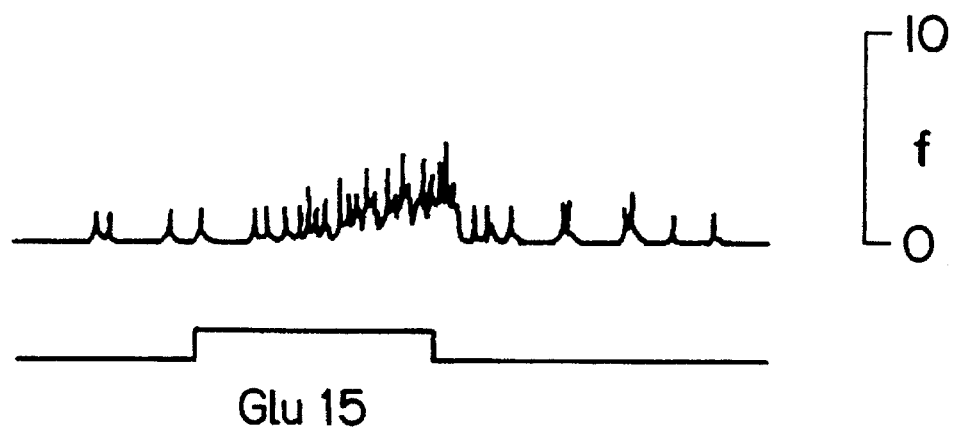
FIG. 1 shows the excitatory effect of L-glutamate on a spontaneously firing fiber in the subsynaptic region of an IHC, a) time frequency histogram of spike-activity during L-glutamate (Glu, 15 nA) application. The length of the perisynaptic release of the agent from the micropipette is indicated by the bar below the histogram; integrating firing frequency immediately at right.
Figure 1B:
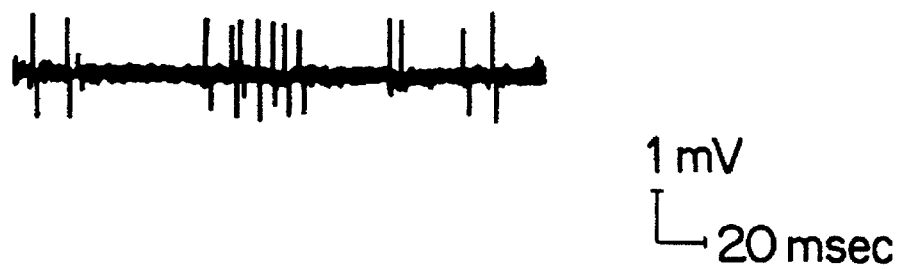

As shown in the original tracing a) of FIG. 1, the glutamate-induced excitatory effect (glutamate: 15 nA for 100 msec) is characterized by an irregular discharge interrupted by bursts. The time frequency reflects the diffusion time of the agent between the micropipette and the synaptic cleft.

Caroverine ejected simultaneously with glutamate (FIG. 2) antagonizes the membrane response to glutamate in an enduring but reversible manner.

In a second series of experiments, the selectivity of the described Caroverine effect was tested by comparing successively the putative antagonism of Caroverine on the glutamate-induced as well as on the acetylcholine-induced postsynaptic excitation of identical dendritic fibers. As shown in FIG. 3, Caroverine applied iontophoretically in an adjusted dosage, which promises a nanomolar concentration of the agent on the synapse, blocked regularly and exclusively the potent glutamate receptors, but exhibited no effect on the membrane response to the excitatory efferent transmitter substance acetylcholine.

Another effective 1-(aminoalkyl)-3-(benzyl)-quinoxaline-2-one derivative is 1-diethylaminoethyl-3-(p-hydroxy)-1,2-dihydroquinoxaline-2-one.

Thus, it is experimentally established that 1-(aminoalkyl)-3-(benzyl)-quinoxaline-2-one derivatives are a potent, reversible and selective class of new glutamate receptor antagonists on the excitatory efferent synapses of the cochlear inner hair cells. The application of Caroverine and its salts, respectively, also in high doses, produces no critical side-effects. As Caroverine does not impair other physiological processes of the CNS its use as a neuroprotective pharmaceutical is straightforward.

The pharmaceutically effective 1-(aminoalkyl)-3-(benzyl)-quinoxaline-2-one derivatives may be incorporated in a conventional systemic dosage form (e.g., oral, rectal or parenteral), such as a tablet, capsule, elixir or injectable. The above dosage forms will also include the necessary carrier material, excipient, lubricant, bulking agent or the like.

The dose administered can be adjusted according to age, weight and condition of the patient. Thus, for oral administration, a satisfactory result may be obtained employing the active substance, e.g., Caroverine, in an amount within the range of from about 0.1 mg/kg to about 5 mg/kg and preferably from about 0.5 mg/kg to about 2 mg/kg. If Caroverine salts are used, then the amounts to be administered should be adjusted according to the increase in molecular weight.

Liquid formulations can also be prepared by dissolving or suspending the active substance in a conventional liquid vehicle acceptable for pharmaceutical administration.

For parenteral administration, the active substance will be employed in an amount within the range of from about 0.1 mg/kg to about 5 mg/kg and preferably from about 0.8 mg/kg to about 2 mg/kg.

The neuroprotective effect of Caroverine was tested in a clinical study with patients who suffered from tinnitus. The etiology of tinnitus can be very different in different patients. One of the most frequent tinnitus type is, however, the cochlear tinnitus. If a functional disturbance between the IHC and the peripheral dendrites of the efferent neurons is deemed to be the initiating, etiological factor, then this is called a "cochlear synaptic tinnitus". A neuroprotective pharmaceutical like Caroverine should therefore have a positive effect on the cochlear synaptic tinnitus.

In a pilot study Caroverine was applied to 72 patients suffering from tinnitus. Caroverine was applied intravenously (160 mg/100 ml physiological NaCl-solution). The real dosage depended on the tinnitus reduction perceived by the individual patient and varied between 70 and 160 mg.

The effectiveness of Caroverine was measured by a subjective rating and tinnitus-matching before and after the infusion of the drug.

66.7% of the patients noted a tinnitus reduction of at least 50% in absolute value immediately after infusion of Caroverine. No sincere side-effects could be observed.

In a double-blind, placebo-controlled clinical study on a group of 15 persons, the cerebral effect of Caroverine was tested by means of electro-encephalogram (EEG)-mapping. The 15 caucasian probands were 7 females and 8 males between 20 and 35 years old (average 27 years). The weight ranged between 53 and 84 kg (average weight: 69 kg) and the height varied between 162 to 186 cm (average height: 175 cm).

Doses of 40 mg or 80 mg of Caroverine or placebo were administered either orally or intravenously for random sampling to the persons in weekly intervals. EEG-tracings as well as recordings of pulse, blood pressure and side effects were carried out 0, 1, 2, 4, 6 and 8 hours after medication.

A multivariate analysis with reference to the EEG-data showed that Caroverine in both doses and independent of the type of administration (orally or intravenously) had a significant effect on the central nervous system in comparison to placebo. With respect to the time-effect-curve no significant differences as to administration could be recorded at the different points in time. The maximum effect was around 1 hour after medication, but even after 8 hours significant differences from placebo were registered.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A method of preventing or treating neurotoxicity in a mammalian patient in need thereof, wherein said neurotoxicity is induced by glutamate or mediated by a glutamate receptor, comprising administering an effective amount of a compound of the formula:

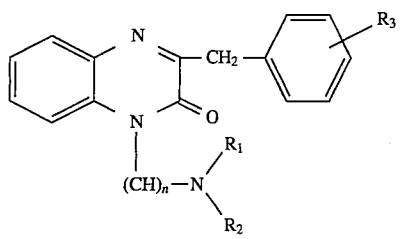

wherein:
- $R_1$ and $R_2$ are each independently hydrogen, methyl, ethyl, propyl, or butyl, or $R_1$ and $R_2$ together are $C_{3-7}$-cycloalkyl;
- $R_3$ is methoxy, ethoxy, hydroxy, hydrogen, $C_{1-4}$-alkyl, or halogen; and
- n is 1, 2, or 3, or a pharmaceutically acceptable salt thereof.

2. A method of claim 1, wherein the compound is 1-diethylaminoethyl-3-(p-methoxybenzyl)-1,2-dihydroquinoxaline-2-one or a pharmaceutically acceptable salt thereof.

3. A method of claim 1, wherein the compound is 1-diethylaminoethyl-3-(p-hydroxybenzyl)-1,2-dihydroquinoxaline-2-one or a pharmaceutically acceptable salt thereof.

4. A method of claim 1, wherein said patient has a functional disturbance of the inner ear.

5. A method of claim 4, wherein the functional disturbance of the inner ear is impaired hearing.

6. A method according to claim 4, wherein the compound is 1-diethylaminoethyl-3-(p-methoxybenzyl)-1,2-dihydroquinoxaline-2-one.

7. A method of claim 1, wherein said patient has post-synaptic tinnitus.

8. A method of claim 7, wherein the compound is administered in an amount of about 70 mg to about 160 mg.

9. A method according to claim 7, wherein the compound is 1-diethylaminoethyl-3-(p-methoxybenzyl)-1,2-dihydroquinoxaline-2-one.

10. A method of claim 1, wherein said patient has a functional disturbance of the retina and is accompanied by loss of vision.

11. A method according to claim 10, wherein the compound is 1-diethylaminoethyl-3-(p-methoxybenzyl)-1,2-dihydroquinoxaline-2-one.

12. A method of claim 1 wherein said patient has a (post)traumatic cerebral lesion, or cerebral damage following oxygen deficiency.

13. A method of claim 1, wherein said patient has a concussion, asphyxiation or oxygen loss due to drowning.

14. A method of claim 1, wherein said patient has Alzheimer's, Huntington's or Parkinson's disease, or Wernicke-Korsakoff or Jakob-Creutzfeldt syndrome.

15. A method of claim 1, wherein said compound is effective in penetrating the blood-brain barrier.

16. A method of claim 1, where said compound is a glutamate receptor antagonist.

* * * * *